United States Patent
Lemonis

(10) Patent No.: US 8,672,925 B2
(45) Date of Patent: Mar. 18, 2014

(54) DEVICE, METHOD, AND CONTROL PROGRAM FOR REFRACTIVE SURGERY

(75) Inventor: Sissimos Lemonis, Schwaig (DE)

(73) Assignee: WaveLight AG, Erlangen (DE)

( * ) Notice: Subject to any disclaimer, the term of this patent is extended or adjusted under 35 U.S.C. 154(b) by 884 days.

(21) Appl. No.: 12/597,139

(22) PCT Filed: Apr. 24, 2008

(86) PCT No.: PCT/EP2008/003311
§ 371 (c)(1),
(2), (4) Date: Apr. 26, 2010

(87) PCT Pub. No.: WO2008/131909
PCT Pub. Date: Nov. 6, 2008

(65) Prior Publication Data
US 2010/0211054 A1   Aug. 19, 2010

(30) Foreign Application Priority Data
Apr. 25, 2007   (EP) ..................................... 07008446

(51) Int. Cl.
*A61B 18/18* (2006.01)
(52) U.S. Cl.
USPC ........................................................... 606/5
(58) Field of Classification Search
USPC ........................................................... 606/5
See application file for complete search history.

(56) References Cited

U.S. PATENT DOCUMENTS

| 4,848,340 | A |   | 7/1989 | Bille et al. |
| 5,231,674 | A | * | 7/1993 | Cleveland et al. ............ 382/117 |
| 5,847,804 | A | * | 12/1998 | Sarver et al. .................. 351/206 |
| 2003/0020874 | A1 | * | 1/2003 | Smith et al. .................... 351/204 |
| 2004/0019346 | A1 | * | 1/2004 | Chernyak .......................... 606/5 |
| 2005/0137586 | A1 |   | 6/2005 | Gray et al. |

FOREIGN PATENT DOCUMENTS

| EP | 1316287 B1 | 2/2007 |
| EP | 1923027 A1 | 5/2008 |
| WO | 03011177 A2 | 2/2003 |

OTHER PUBLICATIONS

Patent Cooperation Treaty—European Patent Office, "Notification of Transmittal of the International Search Report and the Written Opinion of the International Searching Authority, or the Declaration," International Application No. PCT/EPEP2008/003311, Jun. 26, 2008, 11 pages.

* cited by examiner

*Primary Examiner* — Bill Thomson
*Assistant Examiner* — John R Downey
(74) *Attorney, Agent, or Firm* — Haynes and Boone, LLP

(57) ABSTRACT

An apparatus and a method for refractive surgery, in particular LASIK, make provision whereby the apex of the cornea is taken as a basis, as the ablation center, for the refractive procedure. For this purpose, the dependence of the position of the apex on properties of the pupil is determined in the case of the eye to be treated and, from this dependence, measured properties of the pupil are used to calculate the position of the ablation center during the refractive surgery.

19 Claims, 2 Drawing Sheets

DEVICE, METHOD, AND CONTROL PROGRAM FOR REFRACTIVE SURGERY

CROSS-REFERENCE TO RELATED APPLICATION

This application is a United States national phase application of co-pending international patent application number PCT/EP2008/00331, filed Apr. 24, 32008, which claims the benefit of EP Application No. 07 008 446.2 filed Apr. 25, 2007, the disclosure of which is incorporated herein by reference.

BACKGROUND

The invention relates to an apparatus for refractive surgery, to a control program for such an apparatus, and to a method for generating such a control program.

"Refractive surgery" is understood by specialist circles as the alteration of the imaging properties of the optical system "eye" through laser radiation. The laser radiation thus alters the refractive properties of one or more components of the eye. Since it is mainly the cornea that determines the imaging property of the eye, refractive surgery is used, in particular, to perform shaping of the cornea.

A prominent example of such reshaping of the cornea for the purpose of altering its refractive properties is that of LASIK. The present invention relates, in particular, to the LASIK technique. Moreover, the invention is also generally applicable in PRK and EPI-LASIK. The invention can also be applied in the case of use of femtosecond lasers.

In the case of LASIK, according to the prior art, a so-termed ablation profile is determined, i.e. it is calculated, on the basis of measurements on the eye and, if appropriate, other influencing variables, how much tissue (stroma) is to be removed at which location of the cornea, in order that, following the removal, the cornea has an optimum shape for the eye to be treated, i.e. the previously existing optical imaging defects of the eye are, as far as possible, corrected. Various methods are known in the prior art for the said calculation of the ablation profile.

Once the ablation profile has been determined for the eye that is to be treated, it is then calculated how this profile can best be removed (ablated) from the cornea by means of laser radiation. For this purpose, there is calculated a sequence of individual laser pulses, in space and time, which, in interaction with the stroma, effects the required reshaping of the cornea.

The ablation profile is a three-dimensional shape, and corresponds to a volume of the cornea that is to be removed.

The means of so controlling laser radiation by means of a computer that a predefined ablation profile is removed are well known as such in the prior art.

In the case of execution of refractive surgery, the computer controls the laser radiation, for example individual laser pulses ("spots"), over the eye in a space and time sequence in accordance with a control program.

In the case of this control of the laser radiation in respect of the eye, a quite determinant reference quantity is the so-termed ablation centre. The ablation centre is the spatial reference point to which the said spatial sequence of laser pulses relates. In the prior art, the mid-point (the centre) of the pupil is usually used as the ablation centre. The pupil, i.e. the opening left open by the iris, as a diaphragm, for the passage of radiation into the eye, has a relatively sharp contour, and therefore it is suitable for recording by means of a camera and analysed by means of image processing programs. Such recording devices and processing programs are well known as such in the prior art, and the present invention can have recourse thereto to some extent.

During refractive surgery, the eye to be treated is not of a constant size, but rather properties and also the orientation of the eye can change during the procedure. Changes in the orientation of the eye are tracked, according to the prior art, by means of a so-termed eye tracker. An eye tracker traces movements of the eye, usually through the aforementioned recording of the pupil by means of a camera and with subsequent image processing. Movements of the eye are also executed concomitantly by the pupil, and therefore the movements can be determined in this manner, and the control of the laser beam can be matched to such eye movements, i.e. the previously calculated ablation profile is removed with precision, despite eye movements during the operation, which, as a rule, cannot be precluded in a reliable manner.

SUMMARY

As mentioned above, the prior art as a rule uses the centre of the pupil as the ablation centre. The intention of the present invention is to improve this prior art, and in this proceeds from the following considerations:

During refractive surgery, as a general rule the pupil, likewise, does not have a constant size and shape. As a rule, the pupil also does not have a perfect circular shape, but rather it generally has dimensions that are longer in one direction than in another direction. The dimensions of the pupil depend, as is known, on the quantity of incident light, and the eye adapts the cross-section of the pupil as a function of the quantity of incident light. As a general rule, however, change in the size of the pupil also involves a change in the displacement of the pupil centre. In other words, if the pupil widens, this widening is not concentric and, as a general rule, the pupil centre shifts in this case (in the case of a non-circular form, the pupil centre can be understood to be, for example, the centroid of the area). The conditions are rendered yet more complex by the fact that, as a general rule, a change in area of the pupil is also accompanied by a rotation of the non-circular pupil form, this being known in physiology as cyclotorsion.

A series of systematic error sources therefore results if, in the prior art, the pupil centre is used as the ablation centre during refractive surgery.

Firstly, it is applicable that the pupil centre does not lie exactly on the optical axis of the eye. With regard to the optical system "eye", differing axes are defined, the optical axis and the visual axis being of particular importance for the present invention. According to a usual definition, the optical axis joins the centres of curvature of the refractive surfaces of the eye components, i.e. as a rule, it is perpendicular to all refractive surfaces. The visual axis is usually the line that joins the point fixed by the eye and the fovea. As a rule, this line goes through the so-termed nodal point on the rear surface of the lens, doing so at a location at which, as a rule, the optical axis also passes through this point.

Thus, as a rule, the optical axis does not go through the fovea. The angle between the optical axis and the visual axis is typically in the region of 5°.

The invention proceeds from the knowledge that improved refractive-surgery results can be achieved if neither a centre of the pupil nor a point on the optical axis is used as a reference point for ablation, i.e. as a so-termed ablation centre. If the pupil centre is used as the ablation centre, even the above-mentioned displacement of the pupil centre alone, in dependence on the pupil size, regularly results in a systematic error, and it is only by chance, in the case of particular advantageous properties of the eye that happens to be treated, that centring of the ablation on the pupil centre can lead to good ablation results.

Even if the displacement of the pupil centre upon alteration of the size of the pupil were to be taken into account in the determination of the ablation centre, the displacement being physiologically known as such, this would not regularly entail an improvement of the ablation, because the systematic error associated with this choice would be, as it were, carried along.

The above considerations also apply to the case that, for the purpose of calculating the ablation profile and generating the control program for the laser radiation, the eye is measured by means of a wave-front analysis, for example according to Hartmann-Shack or Tscherning, or through topography measurements. In the case of so-termed "standard" ablations, likewise, it is necessary to determine the ablation profile with high precision.

WO 03/011177 A2 teaches the centring of an ablation on the visual axis in relation to the pupil centre.

US 2004/019346 A1 describes a method for ablation on the cornea, wherein the laser radiation is controlled according to the angles between the corneal surface and the laser beam. The respective local angle of incidence of the radiation is used to determine the locally required ablation of the tissue. A thus determined ablation map (ablation profile) does not use the apex of the corneal surface for the purpose of aligning the ablation profile to the apex, in particular not using the dependence of the position of the apex on a property of the pupil.

The invention is based on the object of specifying, for refractive surgery, an ablation centre that is to be determined with relatively simple means and by which improved refractive results can be achieved.

For this purpose, the invention teaches an apparatus for refractive surgery, having the features of claim 1. Furthermore, the invention teaches a control program for such an apparatus, having the features of claim 5.

Preferred developments are described in the dependent claims.

The invention is thus based on the knowledge that improved ablation results can be achieved if, during the surgical procedure, the ablation is centred on the apex of the cornea, which apex is located on the front surface of the cornea.

The apex is the highest point of the cornea, its summit.

As a general rule, the above-mentioned points on the surface of the cornea are not easily determined during the surgical procedure, at least not with the use of known, available means.

The invention therefore teaches the empirical determination, for the eye to be treated, of the functional dependence of the spatial position of the above-mentioned point on the cornea surface (which point is to serve as the ablation centre) on the shape and position of the pupil. As explained above, in the case of refractive procedures, as a general rule the pupil is in any case measured by means of a camera and with sufficient frequency, such that movements of the eye are executed concomitantly by the laser-beam guidance system (eye tracker). If, according to the invention, the pupil is now measured by means of a camera and image processing programs that are even well-known as such, and the dependence of the position, for example the apex, is measured as a function of the pupil data for the eye to be treated, and these measurement results are stored in the computer that subsequently controls the refractive surgery, thus, substantially, the laser beam, the controlling computer can then relate the laser beam, i.e. the ablation profile, to the apex as a reference point (ablation centre). For this purpose, it is necessary only that the pupil, or the iris, be measured during the refractive procedure, which, as stated, is effected for other reasons in any case.

Suitable pupil properties to be measured, which represent the said functional relationship between the selected ablation centre on the cornea and quantities that can be measured during the operation, are, in particular, certain dimensions of the pupil and its shape resulting therefrom. A further improvement is possible in that this functional dependence between the ablation centre and measurement quantities also takes account of properties of the iris. As stated above, the iris usually rotates upon alteration of the pupil size, and this rotation can be identified in that certain structures of the iris rotate, this being identifiable through image processing of the image recorded by means of the camera.

The said functional dependence between the position, e.g. the apex, and properties of the pupil and/or the iris can be stored, for example, in the manner of a memory table in the computer.

The measurement of the functional dependence of the position of the apex (or of another selected ablation centre according to the invention) on measurement data of the pupil, such as, in particular, its size and shape, can be so effected, for example, that (before the refractive surgery, as understood) the apex is determined with the use of appropriate means, for example a topometer, in the case of the eye to be treated. This position of the apex can then be fixed by means of markings on the cornea, which markings preferably are not located directly on the apex. For example, so-termed keratometer marks can be projected close to the apex, which marks define the spatial position of the apex, i.e. the image-processing computer identifies the position of the apex from the markings. The said functional relationship between the properties of the pupil/iris and the apex position is then determined (again, before the actual surgical procedure).

The invention also provides, for example on a data medium, a control program for an apparatus for refractive surgery that comprises the following:
  a laser-beam source,
  means for shaping and guiding the laser beam emitted by the laser-beam source, in relation to an eye to be treated,
  a camera for recording the iris and pupil of the eye,
  a computer, which executes the control program for the purpose of controlling the said means according to an ablation profile,
  the control program:
  including a function of the position of a predefined point of the cornea of the eye in dependence on at least one property of the pupil,
  during the refractive surgery, recording the instantaneous property of the pupil by means of the camera and determining therefrom, by means of the said function, the position of the predefined point of the cornea, and
  aligning the ablation profile to the thus determined position of the point.

The developments described above in relation to the apparatus, particularly in respect of the selection of the ablation centre and the properties of the pupil used for the measurements, can also be applied, in particular, in the case of this control program.

The invention also relates to a method for generating a control program for refractive surgery, by means of which method laser radiation is directed onto or into an eye to be treated, according to a predefined spatial and time sequence, the predefined spatial and time sequence being aligned in relation to a site of the eye, and
  before the refractive surgery, in the case of the eye to be treated, the dependence of the position of the said site on a property of the pupil that can alter during the refractive surgery being determined and stored, the site being located on or in the cornea of the eye.

The aforementioned site of the eye is, in particular, the above-mentioned ablation centre, the apex of the cornea or a point having a fixed distance from the apex. The above-mentioned parameters relating to the pupil properties can also be used in the case of the method, according to the invention, for generating the control program.

BRIEF DESCRIPTION OF THE DRAWINGS

Exemplary embodiments of the invention are explained more fully in the following with reference to the drawings, wherein.

DETAILED DESCRIPTION

Figure 1:
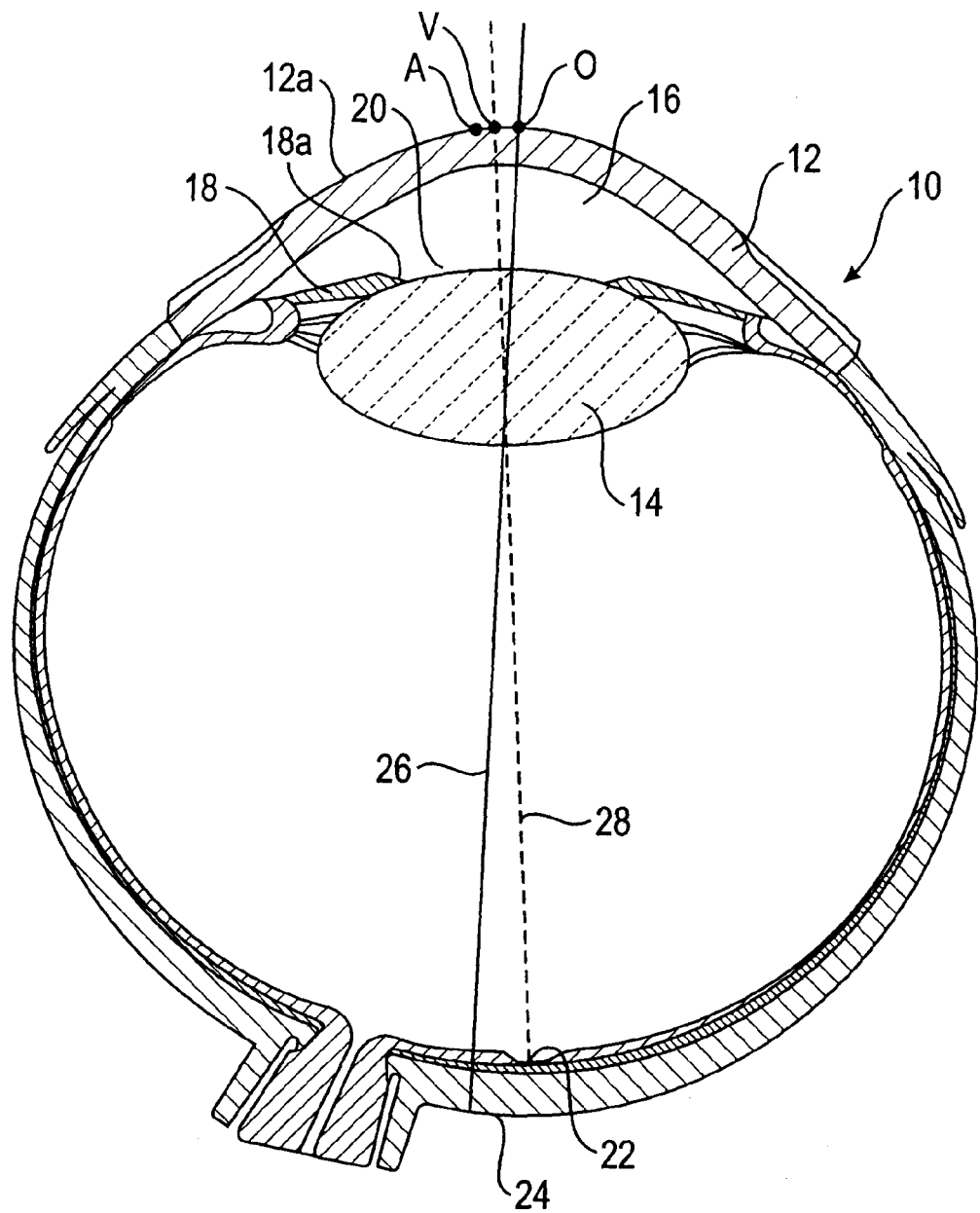
FIG. 1 shows, schematically, a section through an eye, with the axes and points of intersection that are of particular interest in this case.

The saggital section through an eye 10 according to FIG. 1 shows, schematically, a cornea 12, a lens 14, an anterior chamber 16, an iris 18, the edge 18a of which is bounded by a pupil 20, a fovea 22, a macula lutea 24, an optical axis 26 and a visual axis 28.

The optical axis 26 intersects the front surface 12a of the cornea 12 at the location O. The visual axis 28 intersects the front surface 12a of the cornea at the location V.

Regularly, as shown schematically in FIG. 1, the apex A of the cornea 12 is located neither at the location O nor at the location V, such that the point of intersection V of the visual axis is located between the apex A and the point of intersection O of the optical axis with the corneal surface. In this case, as a rule, V is located closer to A than to O. The invention exploits these anatomical regularities.

Figure 2:
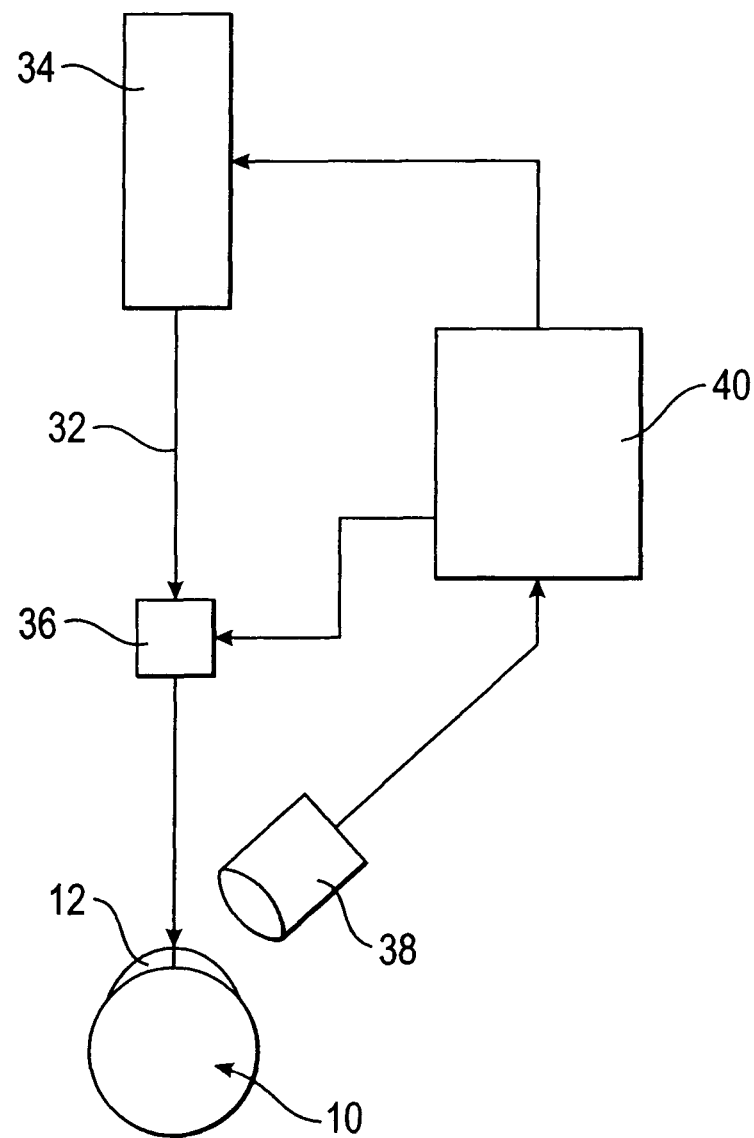
FIG. 2 shows, schematically, an apparatus for refractive surgery.

FIG. 2 shows, schematically, an apparatus for refractive surgery, comprising a laser-beam source 34, which emits a laser beam 32 that, by means of devices 36 for beam shaping and guidance, is directed onto an eye 10 to be treated. A camera, for example an IR camera 38, is used to record, in particular, the pupil and the iris of the eye, and the digital image signal is input to a computer 40.

The computer 40 controls all the components mentioned, thus, in particular, the laser-beam source 34 and the means 36 for beam shaping and guidance. The components described thus far are well known as such in the prior art, and are not explained more fully here.

The ablation profile, explained above, is first determined, in a manner known per se, for an eye to be treated. This is effected through measurement of the eye, e.g. through wavefront analysis. The thus obtained ablation profile is stored in the computer 40. The computer 40 furthermore includes a control program for the purpose of controlling, in particular, the devices 36 for beam shaping and guidance in accordance with the ablation profile. This is likewise well known as such in the prior art.

Firstly, the apex A of the cornea of the eye to be treated is determined, i.e. the spatial coordinates of the apex point A are measured. This can be performed, for example, by means of so-termed keratometer marks, i.e. one or more markings, which define the position of the apex A, are projected on the surface 12a of the cornea, close to the apex A. This measurement of the apex can be effected, for example, by means of a conventional topometer. Thereafter, the coordinates of the apex A can be assumed to be constant for the eye, and they serve as a reference point, i.e. as an ablation centre for a subsequently performed ablation, this reference point remaining invariable even in the case of changing pupil widths and, also, pupil rotation.

In a further step, following the determination of the spatial coordinates of the apex A, the functional dependence of the position of the apex A on the individual pupil movement, thus the change in the pupil width and the in the pupil rotation, is determined for the eye to be treated.

For this purpose, the dependence of the position of the centre on the pupil width is first determined. As explained above, as a general rule a widening of the pupil is not concentric, i.e., as a rule, the pupil centre will have shifted following a widening of the pupil. This dependence of the position of the pupil centre on the pupil width is determined in that differing pupil widths are produced in a stepwise manner, and the coordinates of the pupil centre are determined in relation to each pupil width, with the apex as the reference point. In this case, the variation of the pupil width is effected by altering the incident visible light, such that naturally occurring widening of the pupil is effected (a pharmacological widening of the pupil frequently differs from its natural movement). An infrared camera is then used to determine the respective position of the pupil centre for the various pupil widths, with the previously determined apex as the reference point.

The dependence of the angle of the pupil rotation on the pupil width is determined analogously. In this case, in addition to identifying the pupil centre, the IR camera also identifies the variation of the position of the iris pattern, which provides information concerning the pupil rotation.

In this way, there is determined a function that represents the position of the apex A in dependence on instantaneously occurring properties of the pupil, such as, in particular, the pupil width and the rotational state of the pupil. This empirically measured dependence is stored, for the eye to be treated, in the computer 40, and is then used during the refractive surgery to be performed subsequently, thus, in particular, LASIK, in order to calculate the instantaneous ablation centre. Thus, in the case of this example, the ablation is centred on the apex A.

This is effected, in the case of refractive surgery, in that the pupil 20 and iris 14 of the eye are recorded, by means of the IR camera 38, at a frequency that is sufficiently high to capture movements and pupil variations of the eye with such rapidity that the ablation is adjusted to such variations. The image processing programs stored in the computer 40 use the stored functions, described above, relating to the instantaneous pupil size and pupil position to calculate the coordinates of the apex A, and the computer 40 takes this instantaneous apex A, as the ablation centre, as a basis in the control of the devices 36 for beam guidance, i.e. the individual laser pulses are positioned in accordance with the ablation profile in which the instantaneously measured site of the apex A serves as the ablation centre. This is performed repeatedly, at the said high frequency, during the entire refractive surgical procedure, such that the instantaneous ablation centre always corresponds to the actual state of the eye. In parallel therewith, the "eye tracking", known per se, is performed by means of the camera 38 and the computer 40 during the procedure.

The centring of the ablation on the apex A, as described above, already provides an improved refractive-surgery result, i.e. an improvement of the visual correction.

The invention claimed is:

1. Apparatus for refractive surgery comprising the following:

a laser-beam source;

a camera for recording the iris and pupil of the eye;

a computer, comprising a control program for controlling the said means according to an ablation profile;

wherein the control program:

includes a function of the position of the apex of the cornea of the eye in dependence on at least one property of the pupil;

during the refractive surgery, records an instantaneous property of the pupil by means of the camera and determines therefrom, by means of the function, the position of the apex of the cornea; and aligns the ablation profile to the thus determined position of the apex or of a point of the corneal surface having a fixed distance from the apex.

2. Apparatus according to claim 1, wherein the property of the pupil is at least one or more of its dimensions.

3. Apparatus according to claim 1, wherein the property of the pupil is at least one of its shape and center.

4. Apparatus according to claim 1, wherein the control program also determines, by means of a recorded property of the iris, an instantaneous position of at least one of the apex and a predefined point of the cornea having a fixed distance to the apex.

5. Apparatus for refractive surgery comprising the following:

a laser-beam source;

a camera for recording the iris and pupil of the eye;

a computer which executes a control program for the purpose of controlling said means according to an ablation profile, wherein the control program:

includes a function of the position of the apex of the cornea of the eye in dependence on at least one property of the pupil, during the refractive surgery, records the instantaneous property of the pupil by means of the camera and determines therefrom, by means of said function, the position of the apex of the cornea, and aligns the ablation profile to at least one of the thus determined position of the apex and a point on the corneal surface having a fixed distance from the apex.

6. The apparatus of claim 5, wherein the at least one property of the pupil upon which the position of the apex is dependent as set forth in the function of the control program includes a relationship of the position of the apex to a pupil width.

7. The apparatus of claim 6, wherein the relationship of the position of the apex to the pupil width is determined empirically for the eye to be treated.

8. The apparatus of claim 7, wherein empirically determining the dependency of the position of the apex to the pupil width is determined by altering incident visible light on the eye to be treated.

9. The apparatus of claim 8, wherein the incident visible light on the eye to be treated is altered in a stepwise manner.

10. The apparatus of claim 5, wherein the at least one property of the pupil upon which the position of the apex is dependent as set forth in the function of the control program includes a relationship of the position of the apex to a pupil rotation.

11. The apparatus of claim 10, wherein the relationship of the position of the apex to the pupil rotation is determined empirically for the eye to be treated.

12. The apparatus of claim 11, wherein empirically determining the dependency of the position of the apex to the pupil rotation is determined by identifying variation of a position of an iris pattern.

13. The apparatus of claim 1, wherein the at least one property of the pupil upon which the position of the apex is dependent as set forth in the function of the control program includes a relationship of the position of the apex to a pupil width.

14. The apparatus of claim 13, wherein the relationship of the position of the apex to the pupil width is determined empirically for the eye to be treated.

15. The apparatus of claim 14, wherein empirically determining the dependency of the position of the apex to the pupil width is determined by altering incident visible light on the eye to be treated.

16. The apparatus of claim 15, wherein the incident visible light on the eye to be treated is altered in a stepwise manner.

17. The apparatus of claim 13, wherein the at least one property of the pupil upon which the position of the apex is dependent as set forth in the function of the control program includes a relationship of the position of the apex to a pupil rotation.

18. The apparatus of claim 17, wherein the relationship of the position of the apex to the pupil rotation is determined empirically for the eye to be treated.

19. The apparatus of claim 18, wherein empirically determining the dependency of the position of the apex to the pupil rotation is determined by identifying variation of a position of an iris pattern.

\* \* \* \* \*